(12) United States Patent
Koehl

(10) Patent No.: US 8,487,240 B2
(45) Date of Patent: Jul. 16, 2013

(54) SENSOR

(75) Inventor: Andrew H. Koehl, Cambridge (GB)

(73) Assignee: Owlstone Inc., Norwalk, CT (US)

( * ) Notice: Subject to any disclaimer, the term of this patent is extended or adjusted under 35 U.S.C. 154(b) by 198 days.

(21) Appl. No.: 12/886,679

(22) Filed: Sep. 21, 2010

(65) Prior Publication Data
US 2011/0056371 A1 Mar. 10, 2011

Related U.S. Application Data

(63) Continuation of application No. 11/659,262, filed as application No. PCT/GB2005/050124 on Aug. 2, 2005, now Pat. No. 7,714,278.

(51) Int. Cl.
*H01J 49/00* (2006.01)

(52) U.S. Cl.
USPC ............ 250/282; 250/281; 250/290; 250/292

(58) Field of Classification Search
USPC ................................. 250/281, 282, 290, 292
See application file for complete search history.

(56) References Cited

U.S. PATENT DOCUMENTS

| | | | |
|---|---|---|---|
| 4,821,023 A | 4/1989 | Parks | |
| 5,789,745 A | 8/1998 | Martin et al. | |
| 6,051,832 A | 4/2000 | Bradshaw | |
| 6,107,624 A * | 8/2000 | Doring et al. | 250/286 |
| 6,495,823 B1 | 12/2002 | Miller et al. | |
| 6,512,224 B1 | 1/2003 | Miller et al. | |
| 6,806,463 B2 | 10/2004 | Miller et al. | |
| 7,005,632 B2 | 2/2006 | Miller et al. | |
| 2002/0070338 A1 | 6/2002 | Loboda | |
| 2002/0117617 A1 | 8/2002 | Sinha et al. | |
| 2003/0089849 A1 | 5/2003 | Guevremont et al. | |
| 2003/0155503 A1 * | 8/2003 | Murphy et al. | 250/286 |
| 2003/0201398 A1 | 10/2003 | Perkins | |
| 2004/0047205 A1 | 3/2004 | Hazama et al. | |
| 2004/0222371 A1 | 11/2004 | Hartley | |
| 2005/0145789 A1 | 7/2005 | Miller et al. | |

(Continued)

FOREIGN PATENT DOCUMENTS

| | | |
|---|---|---|
| EP | 0692712 A1 | 1/1996 |
| WO | WO-0164320 A1 | 9/2001 |

OTHER PUBLICATIONS

Miller et al., "A novel micromachined high-field asymmetric waveform ion mobility spectrometer" Sensors and Actuators B, Elsevier Sequoia S.A., Lausanne, CH, 67(3):300-306 (2000).

(Continued)

*Primary Examiner* — Michael Maskell
(74) *Attorney, Agent, or Firm* — Edwards Wildman Palmer LLP; Christopher J. Capelli; Barry Kramer

(57) ABSTRACT

A method and sensor for monitoring chemical species in a gas flow are described. An ionized sample of gas is passed through a flow channel, with a DC electric field applied transverse to the longitudinal axis of the channel. Any electric current produced by the ion flow is measured, with variations in the current being indicative of a change in composition of the gas flow. In certain embodiments, the DC field may be varied over time, to sweep the field voltage. The detected current against field voltage graph may be taken as a profile of a particular gas composition. Variations in the profile again are indicative of a change in gas composition.

12 Claims, 19 Drawing Sheets

U.S. PATENT DOCUMENTS

2005/0263699 A1* 12/2005 Miller et al. .............. 250/292
2006/0055392 A1   3/2006 Passmore et al.
2007/0001123 A1   1/2007 Andrews et al.

OTHER PUBLICATIONS

Krylov, E.V., "Comparison of the planar and coaxial field asymmetrical waveform ion mobility spectrometer" International Journal of Mass Spectrometry 225:39-51 (2003).

International Search Report for PCT/GB2005/050124 mailed on Dec. 10, 2006 (4 pages).

International Preliminary Report on Patentability and the Written Opinion of the International Searching Authority (ISA) for PCT/BG2005/050124) issues on Feb. 6, 2007 (11 pages).

International Search Report dated Oct. 27, 2009 for PCT/GB2009/050466 (6 pages).

* cited by examiner

SENSOR

CROSS REFERENCE TO RELATED APPLICATIONS

This patent application is a continuation of and claims the benefit of priority from International Application No. PCT/GB2009/050466, filed May 6, 2009, which in turn claims the benefit of priority to British Patent Application No. GB 0808344.6, filed May 8, 2008. The disclosure of each of the aforementioned patent applications is incorporated by reference herein in its entirety.

BACKGROUND

1. Field of the Disclosure

The present disclosure relates to a method and a sensor for monitoring chemical species in a gas flow, Aspects of the disclosure relate to methods and devices for monitoring changes in odour; methods and devices for quality control of products; and methods and devices for filtering chemical species.

2. Description of Related Art

Numerous methods exist for monitoring chemical species in a gas flow. Such methods may be used for many different purposes; examples of such purposes include monitoring odours to detect, for example, contamination in food products, or in monitoring changes in air content to detect gas or other chemical leaks.

One of the more versatile methods used is ion mobility spectrometry (IMS), in which differences in the mobilities of ions in an electric field are used to distinguish one species from another. Typically a sample of gas is ionized, and passed through a flow channel which is subject to an electric field. Ions will experience different mobilities within the electric field depending on such factors as their charge, mass, and size. The time taken for ion species to pass through the field and arrive at a detector is calculated, and the resulting spectrum gives an indication of the ion species present in the sample. Generally the detector consists of one or more electrodes at the end of a flow channel or in the walls of the flow channel, with ions being detected once they have transited the flow channel and contacted a detector electrode. The location of the ion along the channel when it is detected can also be used to indicate the time of flight of the ion. The flow channel must therefore be sufficiently long to allow sufficient time of flight for separation of ions.

An alternative to this detection is field asymmetric ion mobility spectrometry (FAIMS). In this, an alternating (RF) asymmetric electric field is established across the flow channel; ions within the channel will be oscillated between the walls of the channel, eventually either passing through the channel or contacting the walls. The RF parameters under which ions will pass through the channel are a function of the differential ion mobility of the ion, so a FAIMS spectrum can provide information regarding the ion species present. This method has the advantage that a long flow channel is not necessary, thanks to the oscillation of ions; however, complex control electronics are needed to take account of this.

Both of these methods are fundamentally similar in that they rely on differences in ion mobility to distinguish ion species (that is, IMS makes use of differences in mobility over time, while FAIMS makes use of differences in differential mobility over frequency or other RF field parameter). The present disclosure, by contrast, aims to provide a simpler, less complex method for detecting or monitoring ion species. This is achieved, in part, through the determination simply of ion mobility, rather than differences in ion mobility; this allows the use of a DC electric field, and a relatively short flow channel while still retaining sufficient discriminatory power for certain desired applications.

SUMMARY OF THE DISCLOSURE

Advantages of the present disclosure will be set forth in and become apparent from the description that follows. Additional advantages of the disclosure will be realized and attained by the methods and systems particularly pointed out in the written description and claims hereof, as well as from the appended drawings.

According to a first aspect of the disclosure, there is provided a method for monitoring chemical species in a gas flow. The method includes ionizing a sample of gas, passing the ionized sample through an ion flow channel along a longitudinal axis thereof, the channel being subject to a DC electric field which is transverse to the longitudinal axis of the channel, monitoring over time the electric current at a detector electrode arranged to intercept at least some of the ions, with a change in current being indicative of a change in the composition of chemical species in the gas flow.

Preferably, embodiments of the present disclosure thus monitor chemical composition simply by detecting electric current at a detector electrode. It is important to note that this method does not rely on time of flight of chemical species; they are simply either passed or not passed by the ion flow channel. It is therefore mobility of ion species which is indirectly measured, rather than differences in mobility which is the case with alternative methods. This also permits the use of a relatively short ion flow channel, since it is not necessary to allow ions of different mobilities to separate as they pass along the channel.

The method may further comprise the steps of varying the DC field over time; and comparing monitored electric current with the DC voltage. This effectively sweeps the DC electric field voltage over time; as each sweep is carried out, certain ion species will either pass or not pass through the ion channel, and be detected (or not detected) as current at a detector electrode. The resulting current against voltage comparison (whether as a graph, or purely statistically) can be taken as being indicative of a particular profile of chemical species. This is considered more sensitive than a method without voltage sweeps, since information regarding the ion composition of the gas may be derived from the height, variance, kurtosis, and other statistical parameters of the current against voltage graph. Variation in any one of these parameters may indicate a change in the ion composition of the gas. The variation is preferably generally continuous, although in some embodiments the DC field may be stepped or switched on and off. The DC field may in certain embodiments be periodically reversed.

The DC field may be repeatedly cycled over time; successive cycles may be compared with one another to monitor for changes in ion composition. Where the DC field is varied, preferably the voltage of the field may be varied. Alternatively, or in addition, the frequency may be varied.

The step of detecting current flow may include detecting ions which have passed completely through the ion flow channel; or may include detecting ions which do not pass through the ion flow channel. In the former embodiment, the detector electrode may be located generally transverse to the longitudinal axis of the ion flow channel; and preferably outside the ion flow channel. In the latter embodiment, the detector electrode may comprise one or more walls of the ion flow channel. The step of ionizing the sample of gas may include subjecting the sample to ionizing radiation; alternatively, other means for ionizing the sample may be used.

The step of passing the ionized sample through the flow channel may include the use of a pump, for example a diaphragm pump, to drive the sample flow. The pumping may be continuous or intermittent. Passing the ionized sample through the flow channel may also or instead comprise the use of a carrier gas flow, for example an inert gas, to entrain the sample gas.

The method may further include the step of obtaining the sample of gas. The sample may be taken from, for example, environmental air; gas adjacent a food product or products; odour samples; and so forth.

The method may still further include the step of processing data relating to the monitored current to obtain further information on the ions. The processing may include one or more of: filtering the data to smooth it; removing outliers and or offsets from the data; normalizing the data; and extracting statistical parameters from the data.

The step of monitoring over time the electric current may include comparison of one or more of the following characteristics: amplitude; variance; kurtosis; and other statistical parameters. These characteristics may be obtained from a graphical or virtual plot of the monitored current; or may be obtained using appropriate statistical methods. One such appropriate method, which will be known to the skilled person, is the method of moments.

The method may further include the step of alerting a user to a variation in the monitored current. In certain embodiments, such an alert may only take place if the variation is beyond a predetermined amplitude, or a predetermined percentage of the average monitored current. Alternatively, other conditions may be required for an alert to take place; for example, a change in a predetermined direction (increase or decrease of the current). The alert may take the form of an audible alarm; or may be a graphical or visual alert, or notification by SMS, email, or the like. Other possibilities will occur to the skilled person.

According to a further aspect, there is provided a method for monitoring a change in air quality, the method including ionizing a sample of air, passing the ionized sample through an ion flow channel along a longitudinal axis thereof, the channel being subject to a DC electric field which is transverse to the longitudinal axis of the channel, and monitoring over time the electric current at a detector electrode arranged to intercept at least some of the ions, with a change in current being indicative of a change in the air quality in the sample.

The disclosure also provides a method for monitoring changes in odours, comprising monitoring chemical species in a sample as described. Also provided is a method for monitoring quality of products being produced, the method including obtaining a sample of gas from the vicinity of the products being produced, ionizing the sample of gas, passing the ionized sample through an ion flow channel along a longitudinal axis thereof, the channel being subject to a DC electric field which is transverse to the longitudinal axis of the channel, and monitoring over time the electric current at a detector electrode arranged to intercept at least some of the ions, with a change in current being indicative of a change in the composition of chemical species in the gas flow, and hence quality of products being produced.

The disclosure still further provides a method of filtering chemical species, the method including ionizing a sample of gas containing a mixture of chemical species and passing the ionized sample through an ion flow channel along a longitudinal axis thereof, the channel being subject to a DC electric field which is transverse to the longitudinal axis of the channel, such that at least some of the ions are deflected sufficiently to contact a wall of the ion flow channel, with any remaining ions passing through the length of the flow channel.

According to a further aspect of the present disclosure, there is provided a sensor for monitoring chemical species in a gas flow. The sensor includes means for ionizing a sample of gas, an ion flow channel defining a longitudinal axis along which ions may pass, a pair of electrodes for providing a DC electric field across the ion flow channel transverse to the longitudinal axis of the channel, and a detector electrode arranged to intercept at least some ions passed along the flow channel.

The sensor may further include an electrode driver for driving the operation of the electrode pair. Conveniently, the electrode driver also preferably includes means for varying the amplitude of the electric field over time. Preferably only one pair of electrodes is provided. In certain embodiments, multiple individual sensors, each of which has only one pair of electrodes, may be combined. The detector electrode may be located at or beyond an end of the ion flow channel. Alternatively, the detector electrode may be located on or may include a wall of the ion flow channel. Where this is the case, the detector electrode may preferably be a member of the electrode pair.

Preferably, the ion flow channel is relatively short; for example less than 4 mm, less than 3 mm, less than 2 mm, less than 1 mm, or less than 0.5 mm in length. In certain embodiments, a plurality of ion flow channels may be provided. These may be provided as a plurality of channels formed in a substrate, for example a substrate of resistive silicon or the like. The channels may be formed by micromachining, by etching, or by other suitable techniques. The channels may be formed by a plurality of interdigitated fingers; conveniently by a pair of electrodes each having a plurality of fingers which are interdigitated with fingers on the other of the electrode pair.

In preferred embodiments, the sensor may further include a microprocessor or other computing device for monitoring the current at the detector electrode. The computing device may also be configured to repeatedly sample the current, and/or to compare monitored current over time. The sensor may include a graphical display for displaying monitored current. The sensor may include an alarm which is configured to activate when the monitored current deviates beyond a certain range, either absolutely or relative to previously monitored current.

In alternative embodiments of the disclosure, however, no microprocessor is provided, and the sensor merely includes means for connecting the sensor to such a microprocessor. That is, the sensor may be provided as a component to be integrated into a sensor device. The means for ionizing may include a source of ionizing radiation, an ultraviolet light source, an arc generator, a corona discharge device, or the like. The sensor may further include a pump for driving a gas flow through the ion flow channel.

A further aspect of the disclosure provides an apparatus for monitoring air quality. The apparatus includes means for ionizing a sample of air, an ion flow channel defining a longitudinal axis along which ions may pass, a pair of electrodes for providing a DC electric field across the ion flow channel transverse to the longitudinal axis of the channel, and a detector electrode arranged to intercept at least some ions passed along the flow channel.

The disclosure also provides a device for filtering ions, the device comprising means for ionizing a sample of gas; an ion flow channel defining a longitudinal axis along which ions may pass; a pair of electrodes for providing a DC electric field across the ion flow channel transverse to the longitudinal axis of the channel; and a filter electrode arranged to intercept at least some ions passed along the flow channel.

Further provided is a gas sensor device, comprising means for ionizing a sample of gas; an ion flow channel defining a longitudinal axis along which ions may pass; a pair of electrodes for providing a DC electric field across the ion flow channel transverse to the longitudinal axis of the channel; and a detector electrode arranged to intercept at least some ions passed along the flow channel.

It is to be understood that the foregoing general description and the following detailed description are exemplary and are intended to provide further explanation of the disclosed embodiments.

The accompanying drawings, which are incorporated in and constitute part of this specification, are included to illustrate and provide a further understanding of the method and system of the disclosed embodiments. Together with the description, the drawings serve to explain principles of the disclosed embodiments.

DETAILED DESCRIPTION OF PREFERRED EMBODIMENTS

Reference will now be made in detail to the present preferred embodiments of the disclosure, examples of which are illustrated in the accompanying drawings. The method and corresponding steps of the disclosed embodiments will be described in conjunction with the detailed description of the system.

Figure 1:
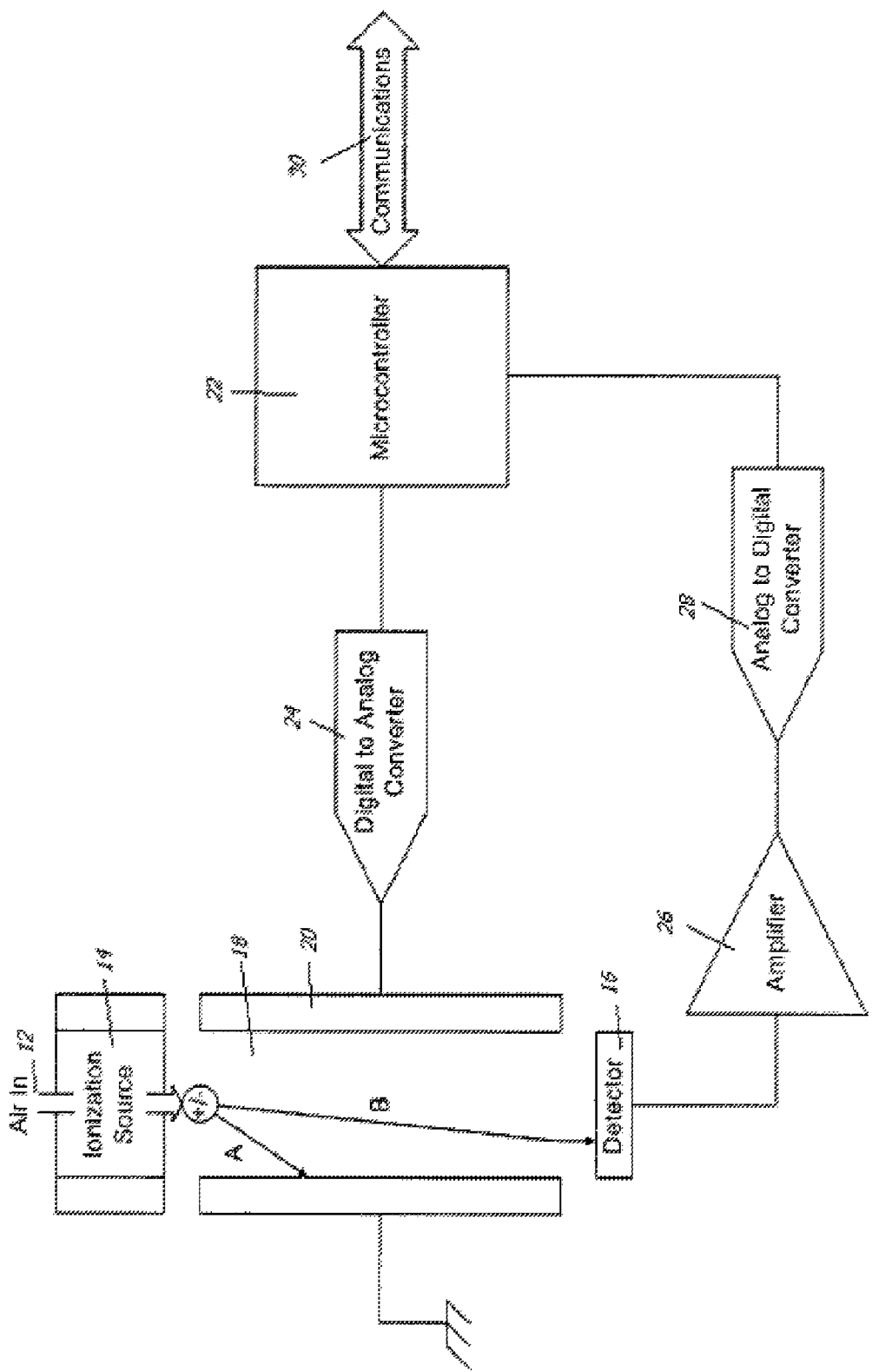
FIG. 1 shows a schematic diagram of a first embodiment of a device for monitoring chemical species in a gas flow.

Referring first of all to FIG. 1, this shows a schematic diagram of an embodiment of a device for monitoring chemical species in a gas flow. The device 10 includes an air inlet 12, an ionization source 14, and a detector electrode 16. Located between the detector electrode 16 and the ionization source 14 is an ion flow channel 18, defined by a pair of electrodes 20. The electrodes 20 are coupled to a microcontroller 22 via a digital to analog converter 24; the microcontroller operates to drive the electrodes 20 to generate a DC electric field across the ion flow channel. The microcontroller 22 is also coupled to the detector electrode 16 via an amplifier 26 and an analog to digital converter 28. The microcontroller 22 feeds to a communications link 30.

Typically, the electrodes 20 are formed from a wafer of high resistivity silicon or the like; they may be etched in a similar manner to conventional silicon chip components. Alternatively other constructions may be used. For example, MEMS fabrication in metal, or a printed circuit board (PCB) with a metallized slot, or the like. In certain embodiments more than one ion flow channel may be provided; specifically, multiple flow channels may be formed in a single wafer.

In use, the exemplary device operates as follows. Ambient air is taken into the inlet 12 and passed through the ionization source 14. This source may be a radioactive source, an ultraviolet light source, a corona discharge device, or the like. Once adjacent to the source, chemical species in the air sample are ionized, such that they carry an electric charge. The ions are then passed through the ion flow channel 18, for example by being carried in a flow of pumped gas. The ion flow channel 18 is subject to a DC electric field generated by the electrodes 20 which are being driven by the microcontroller 22. The field is generally transverse to the longitudinal axis of the ion flow channel 18. As ions are blown through the flow channel, the electric field transports them toward one of the channel sidewalls (that is, the electrodes 20). Ions that impact a sidewall are annihilated, while ions which do not contact a sidewall pass through the channel, and contact the detector electrode 16. At zero volts, most of the ions make it through the channel; conversely, at a high enough voltage none of the ions make it through the channel. The device illustrated in FIG. 1 therefore acts somewhat like a low pass filter, in that ions of low mobility will be deflected less than ions of high mobility, and hence will pass through the channel to the detector electrode 16. Signals from the detector electrode 16 are amplified 26, converted to digital 28, and passed to the microcontroller 22, which monitors the detected current flow over time.

In preferred embodiments of the disclosure, the microcontroller 22 causes the electric field generated by the electrodes 20 to cycle from low to high over time; the signal detected by the detector electrode 16 is then compared with the magnitude of the generated electric field, and the resulting current versus voltage graph used as a characteristic of a particular sample. Over successive cycles the signal graphs may be compared by the microcontroller, and any differences taken as being indicative of a change in the monitored sample.

It is important to note that the time taken by the ions to travel through the ion flow channel, or indeed to contact the sidewall of the channel, is not monitored and is not of relevance for the performance of the device. Thus, the device does not generate an ion mobility spectrum, useful for comparing characteristics of different ions. (The data may however be used to infer characteristics relevant to ion mobility.) Instead, the device generates a more general analysis of the composition of a sample, with particular utility in monitoring changes between samples taken over time.

Figure 2:
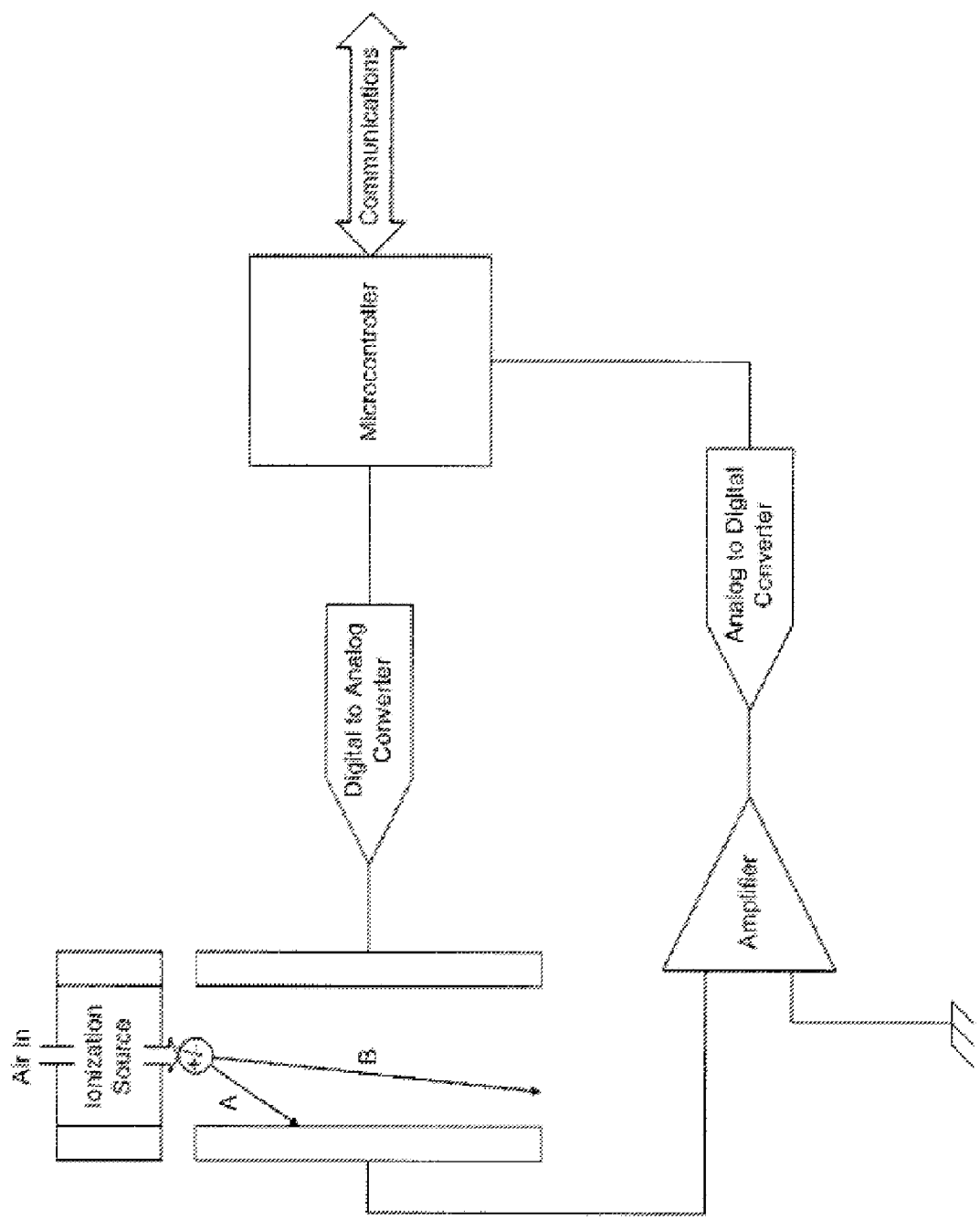
FIG. 2 shows a schematic diagram of a second embodiment of a device for monitoring chemical species in a gas flow.

An alternative construction for the exemplary device of the present disclosure is shown in FIG. 2. This is generally similar to the device of FIG. 1, with the exception that the detector electrode 16 forms one of the sidewalls of the ion flow channel 18 and also acts as one of the paired electrodes 20 used to generate a transverse DC electric field. In this embodiment, ions of high mobility will be deflected into the sidewall, and hence into the detector electrode 16, while ions of low mobility will pass through the ion flow channel without deflection, and so will not be detected. In this way the device acts somewhat like a high pass filter.

Figure 3:
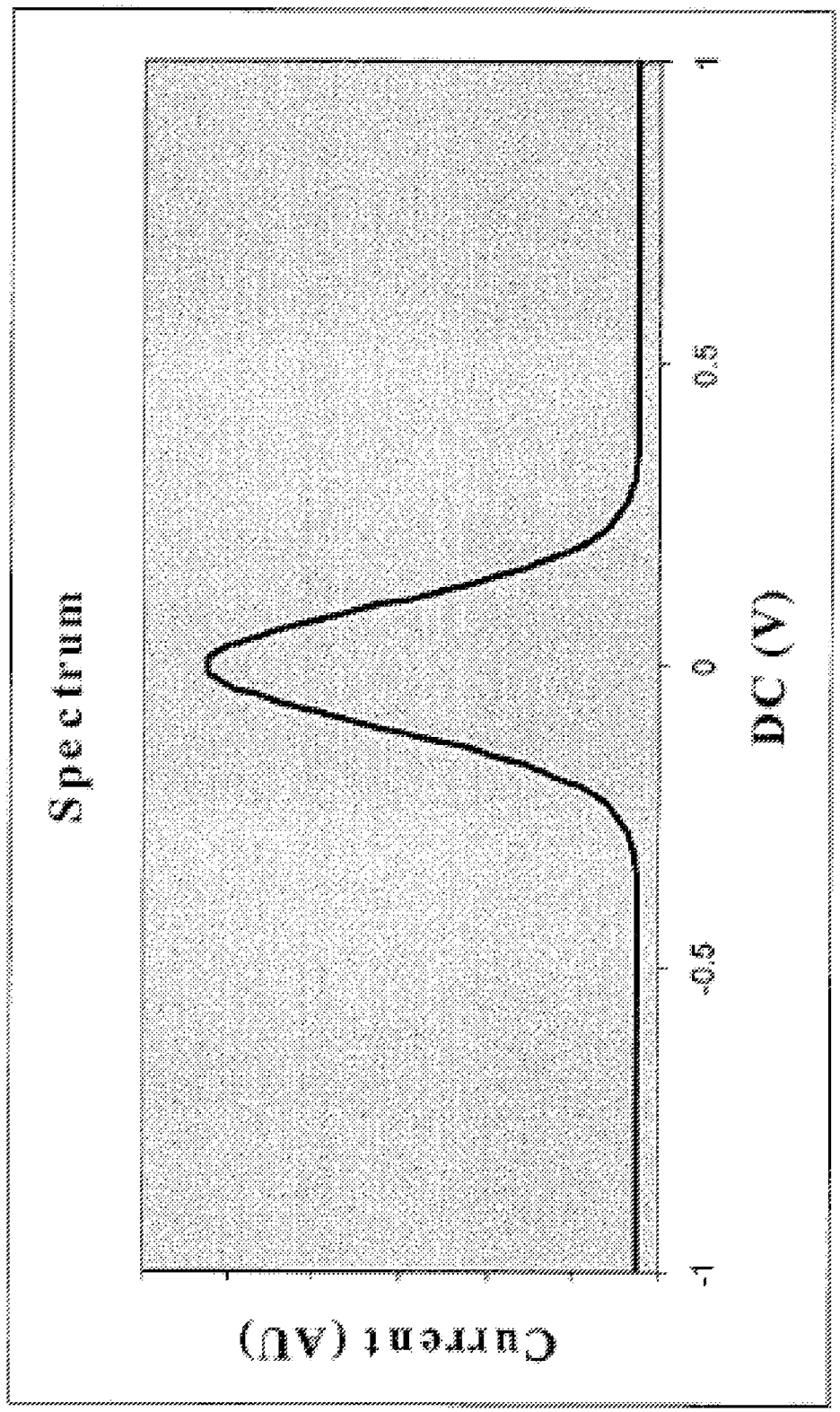
FIGS. 3 and 4 show hypothetical spectra obtained from single and multiple chemical species using the method of the present disclosure.
Figure 4:
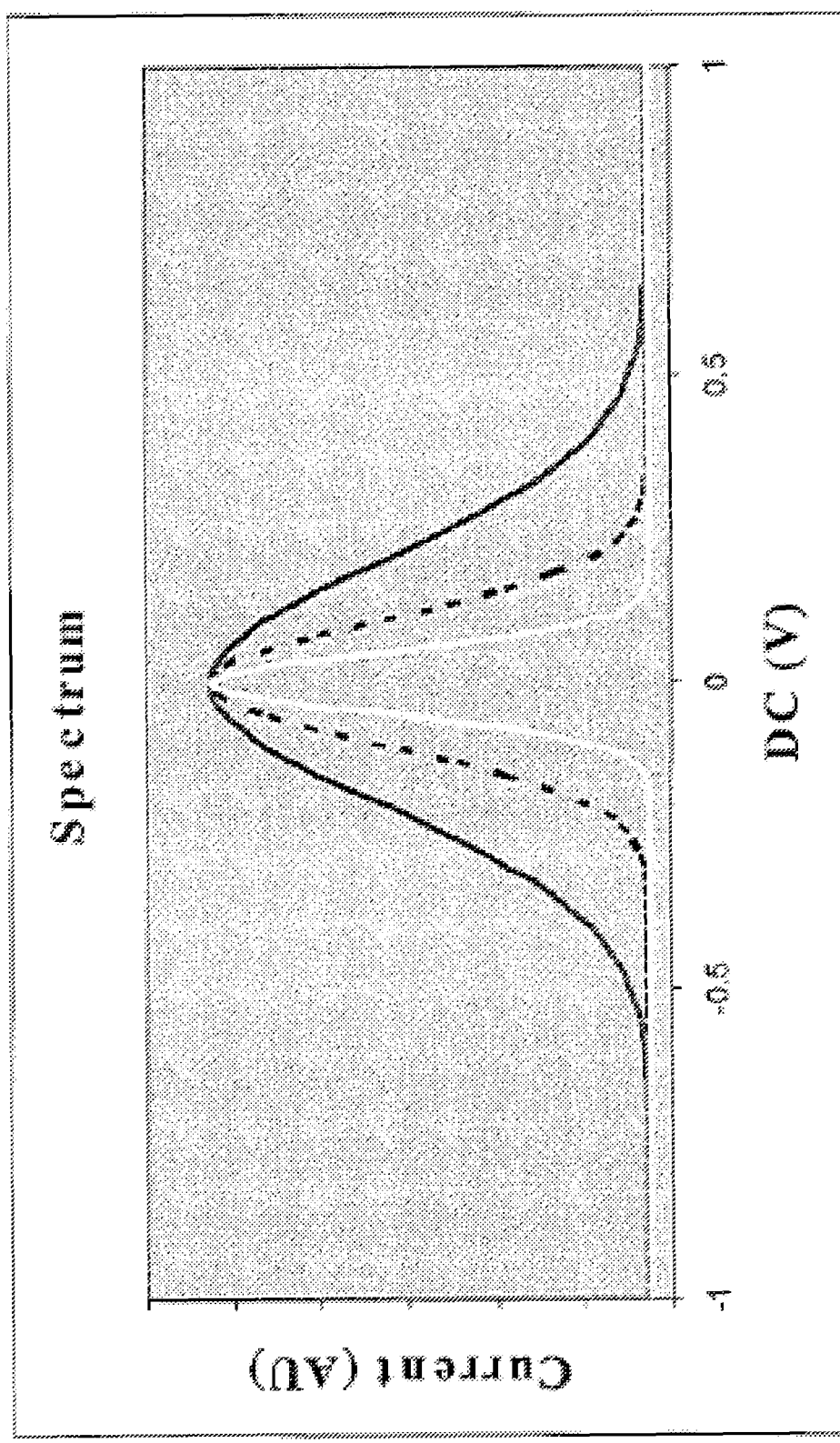

Hypothetical spectra obtained from the device of FIG. 1 are shown in FIGS. 3 and 4. FIG. 3 shows the current against voltage plot from a single ion species. Any one species of ion produces a perfectly Gaussian shaped peak. The standard deviation (i.e. width) of the peak corresponds to ion mobility. The amplitude of the peak corresponds to ion concentration. The kurtosis (i.e. pointedness) of the peak indicates whether multiple species of ions are present, as a sum of dissimilar Gaussians may be pointed or blunt. A plot from multiple species is shown in FIG. 4; higher mobility ions produce narrower peaks, while lower mobility ions produce broader peaks.

The low resolution of the technique coupled with the fact that there are always many species of ion present makes inferring ion mobility from the sample data very difficult. Of course, if only a single ion species were present at any one time (i.e., using a GC and UV ionization) this might be possible; however, the cruder method described herein in fact finds many potential applications. In particular, what the method can do is provide a simple analysis of the overall smell of an odour. It is especially well suited to detecting changes in a smell as well as characterizing how the smell has changed.

Initial testing was carried out to obtain actual sample data, and to explore the sensitivity of the technique. The initial experiment demonstrated that different substances produce peaks with different characteristic widths and heights. It was also demonstrated that these parameters could be used for identification purposes. A simple graphical application was developed that could be calibrated to the smell characteristics for several items. When run, it would correctly identify the smell present. The application adjusted for changes in concentration by memorizing the width-vs-amplitude trajectory that the peak took with changing analyte concentration. We demonstrated that this approach was feasible.

The crude data was subjected to several data processing steps in order to facilitate analysis and comparison. First, the data was filtered to smooth out pump noise and other random noises. Second, the horizontal and vertical offsets were removed. Third, the height of the peak was extracted. Fourth, the peak height was normalized. Fifth, the width of the peak was extracted. Finally, the extracted values were plotted on a width-versus-height plot. It should be noted that other data processing techniques may be used; for example, statistical methods may be used to obtain standard deviation and amplitude measurements from the raw data.

A spectrometer was developed with the following properties: postcard size footprint; continuous scanning capability; less than 1 second required per scan; power consumption less than 100 milliwatts; capable of both positive and negative mode scans.

Figure 5:
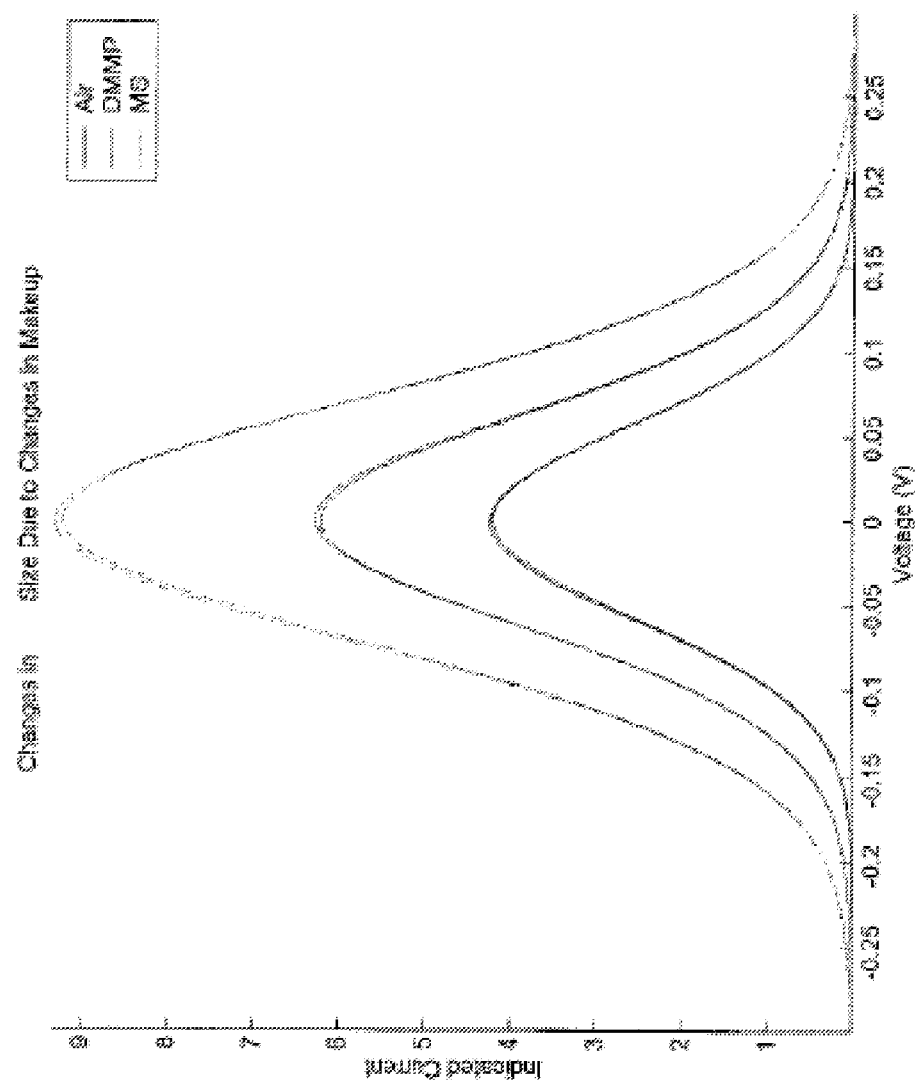
FIGS. 5 and 6 show spectra obtained from three test samples containing chemical species using the method of the present disclosure.
Figure 6:
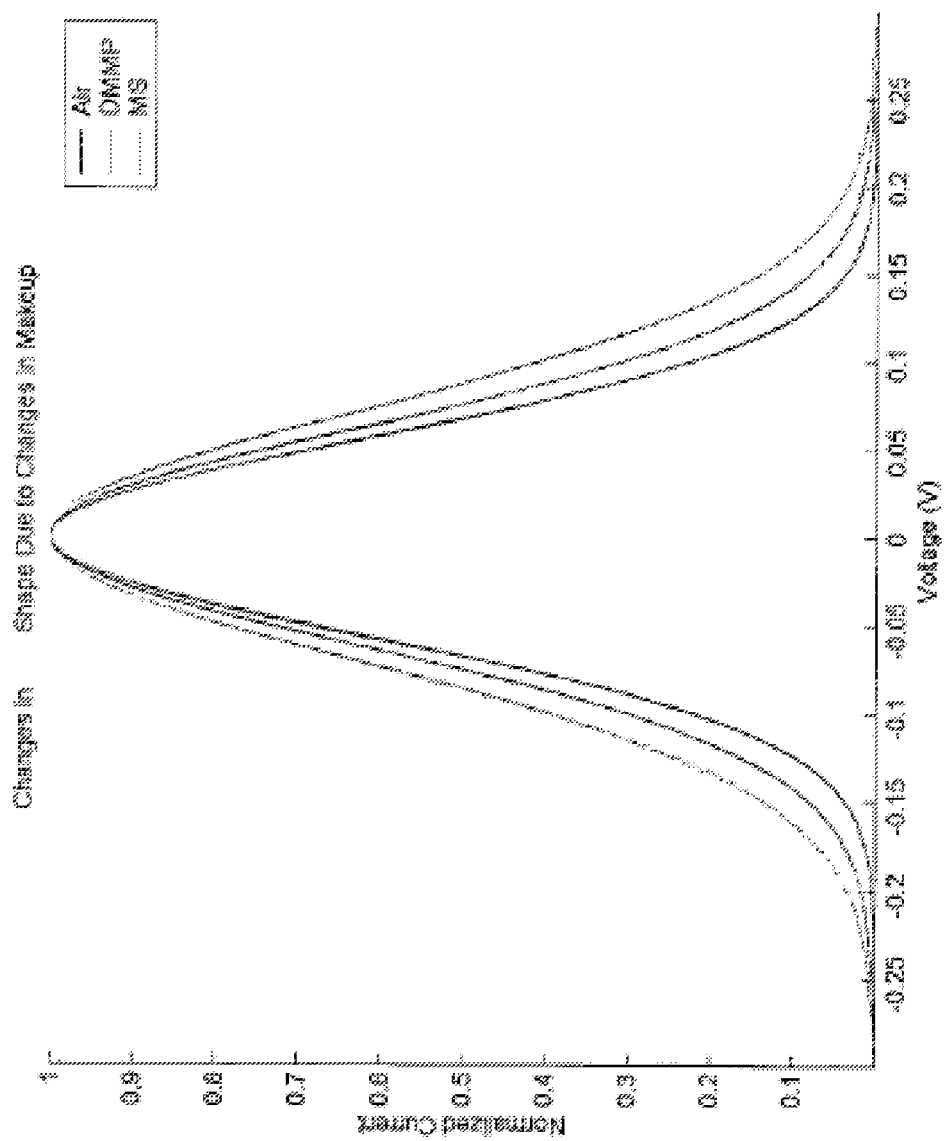

FIGS. 5 and 6 show spectra obtained from an experiment comparing changes in composition of samples. Three different air samples were used (air vs. DMMP [dimethyl methyl phosphonate] vs. MS [methyl salicylate]). FIG. 5 shows the filtered and adjusted spectra; FIG. 6 shows normalized spectra. It can be seen that there is a significant difference in the shape and size of a curve versus chemical composition. As predicted by theory, a lower mobility compound results in a broader curve (MS), while a higher mobility compound results in a narrower curve (DMMP).

Figure 7:
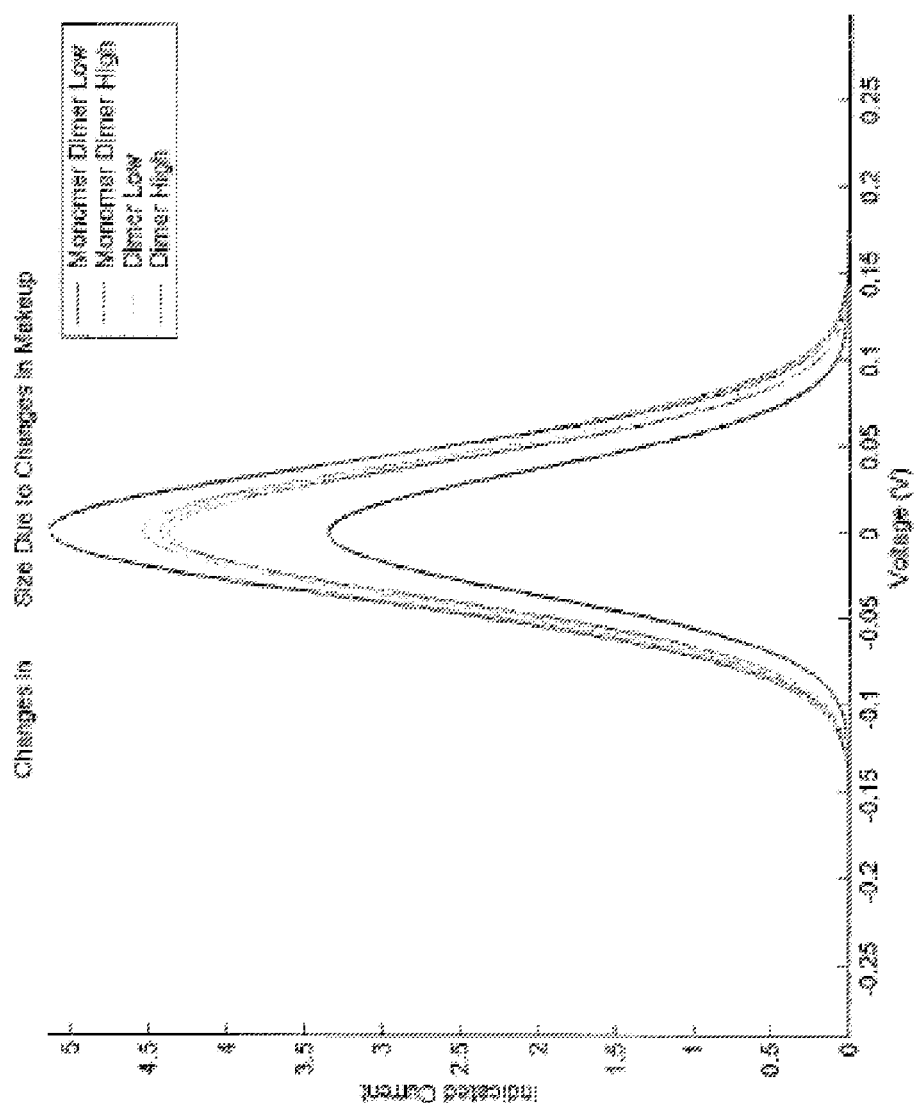
FIGS. 7 and 8 show spectra obtained from a single compound at different concentrations using the method of the present disclosure.
Figure 8:
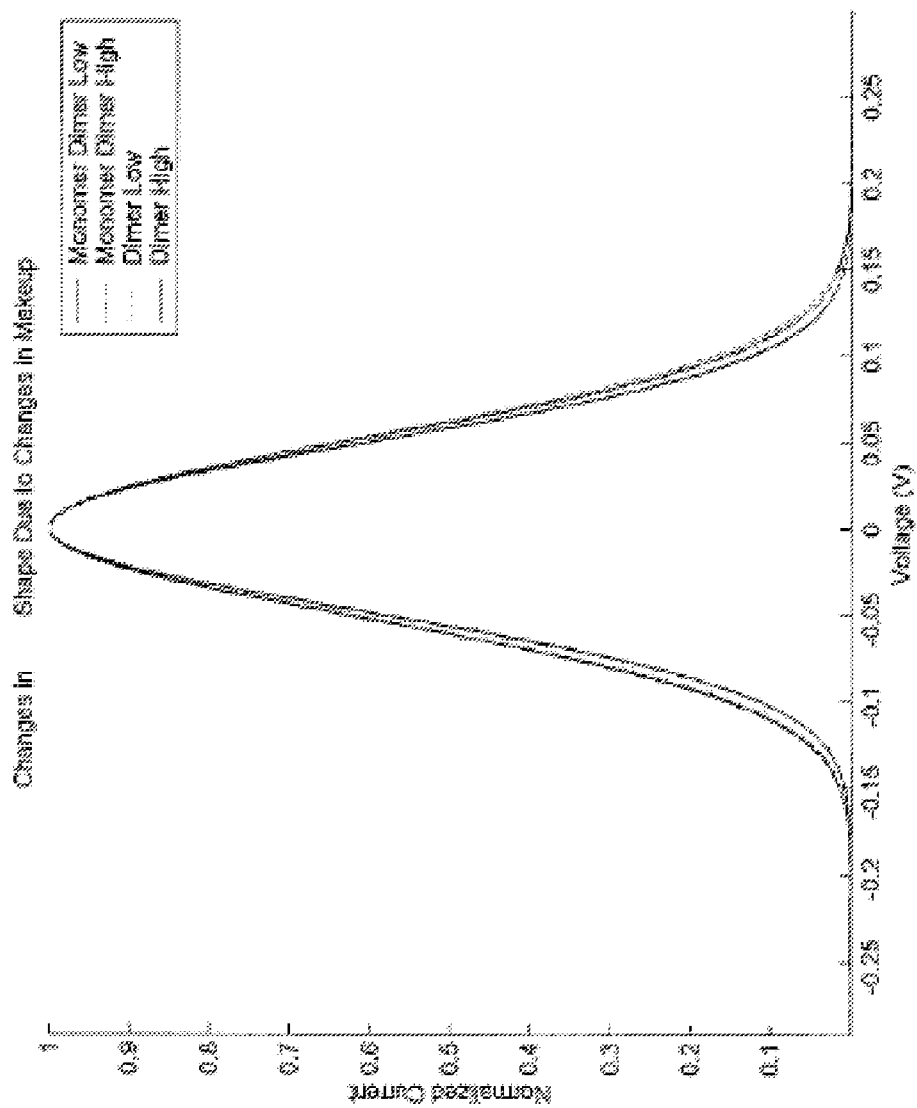

We then tried varying the concentration of a single compound (DMMP). FIGS. 7 and 8 show the results; again, FIG. 7 shows filtered and adjusted spectra, while FIG. 8 shows normalized spectra. Simultaneous FAIMS (field asymmetric ion mobility spectrometry) spectra were used to identify monomer and dimer makeup. There is a detectable difference in the size and shape of a curve versus the analyte concentration. The difference in shape is much less than when the analyte composition is varied. This is a useful property since changes in concentration do not alter the shape to the extent that it looks like a different compound, yet a change is detected. Increasing the concentration yields increasingly broader curves, as expected. A higher concentration results in a greater dimer and lower monomer concentration. The dimer has a lower mobility (and hence broader peak) than the monomer.

Figure 9A:
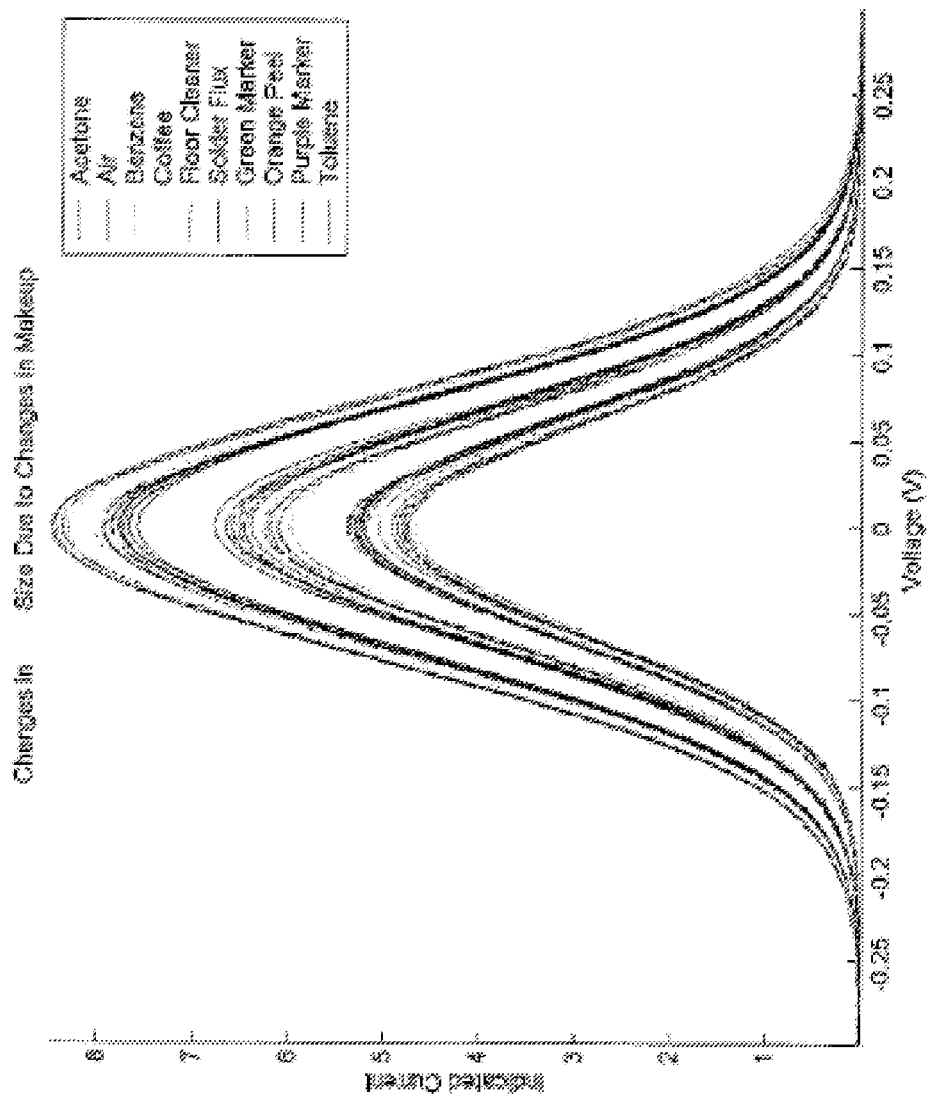
FIGS. 9 and 10 show spectra obtained from ten different samples using the method of the present disclosure.
Figure 9B:
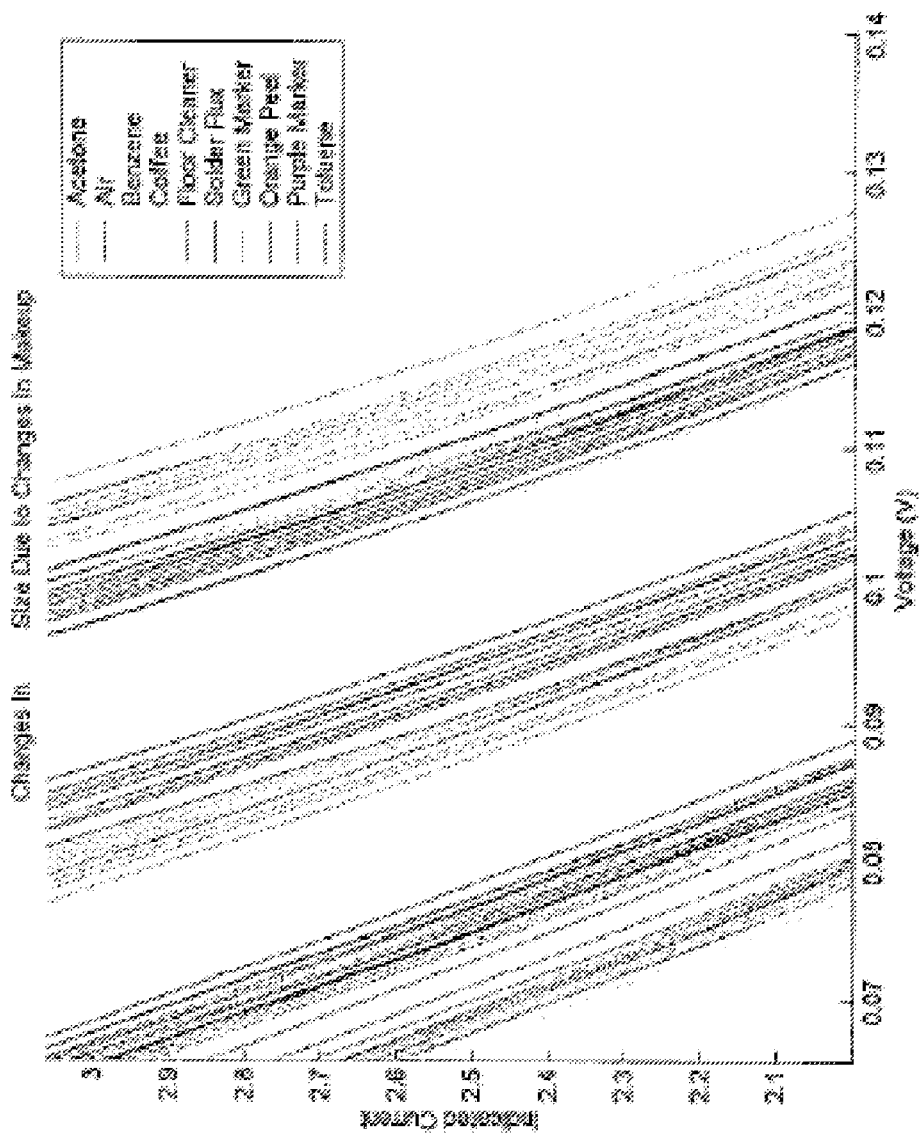
Figure 10A:
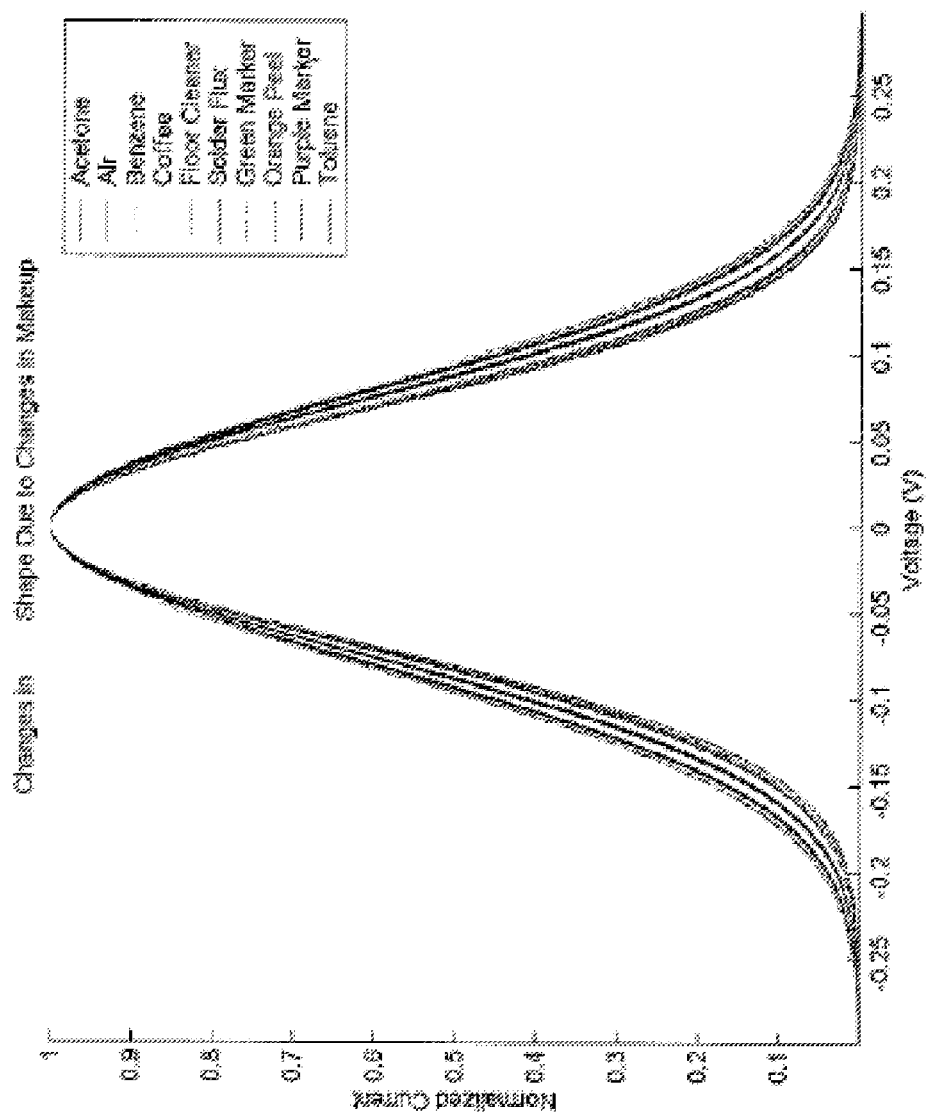
Figure 10B:
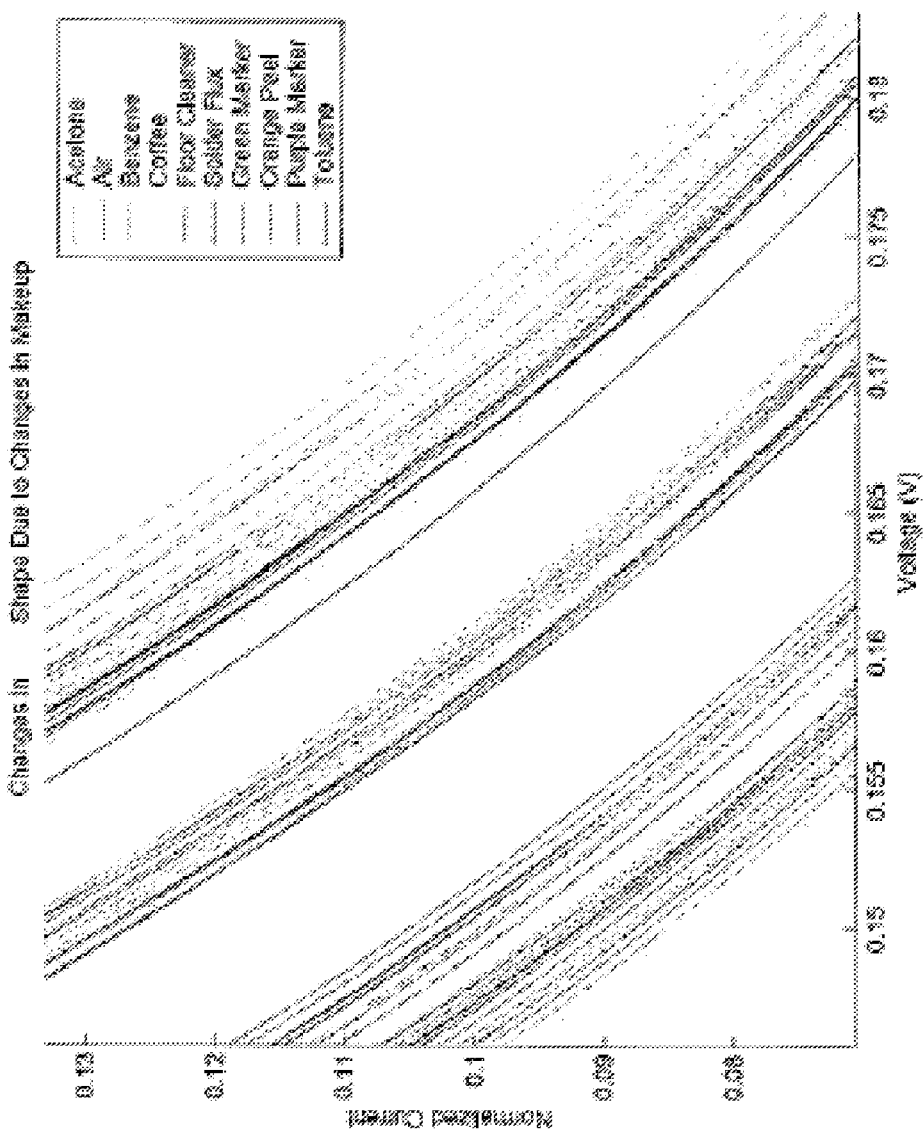

Next, we tried a comparison of ten different substances. FIGS. 9 and 10 show the results; again, FIG. 9 shows filtered and adjusted spectra, while FIG. 10 shows normalized spectra. FIGS. 9b and 10b are enlargements of portions of the spectra of FIGS. 9 and 10, respectively. Samples were collected from the ambient air headspace of a bottle and mixed into a makeup flow consisting of dry filtered air. All substances exhibited a unique curve shape. The list of substances is: green marker, acetone, solder flux, purple marker, floor cleaner, orange peel, coffee, air, benzene, toluene. There is a rough correlation between curve shape order and curve size order. Coffee, orange peel, and air at first appear to have identical spectra; however, an analysis of curve shape reveals that their spectra are distinct.

A further experiment (data not shown) was carried out using the same ten substances, but without the makeup flow of filtered air. Samples were instead collected from the headspace of a bottle using only unfiltered ambient air. The results were broadly similar to those of the previous experiment, demonstrating that the device can be used to distinguish samples taken directly from ambient air.

Figure 11:
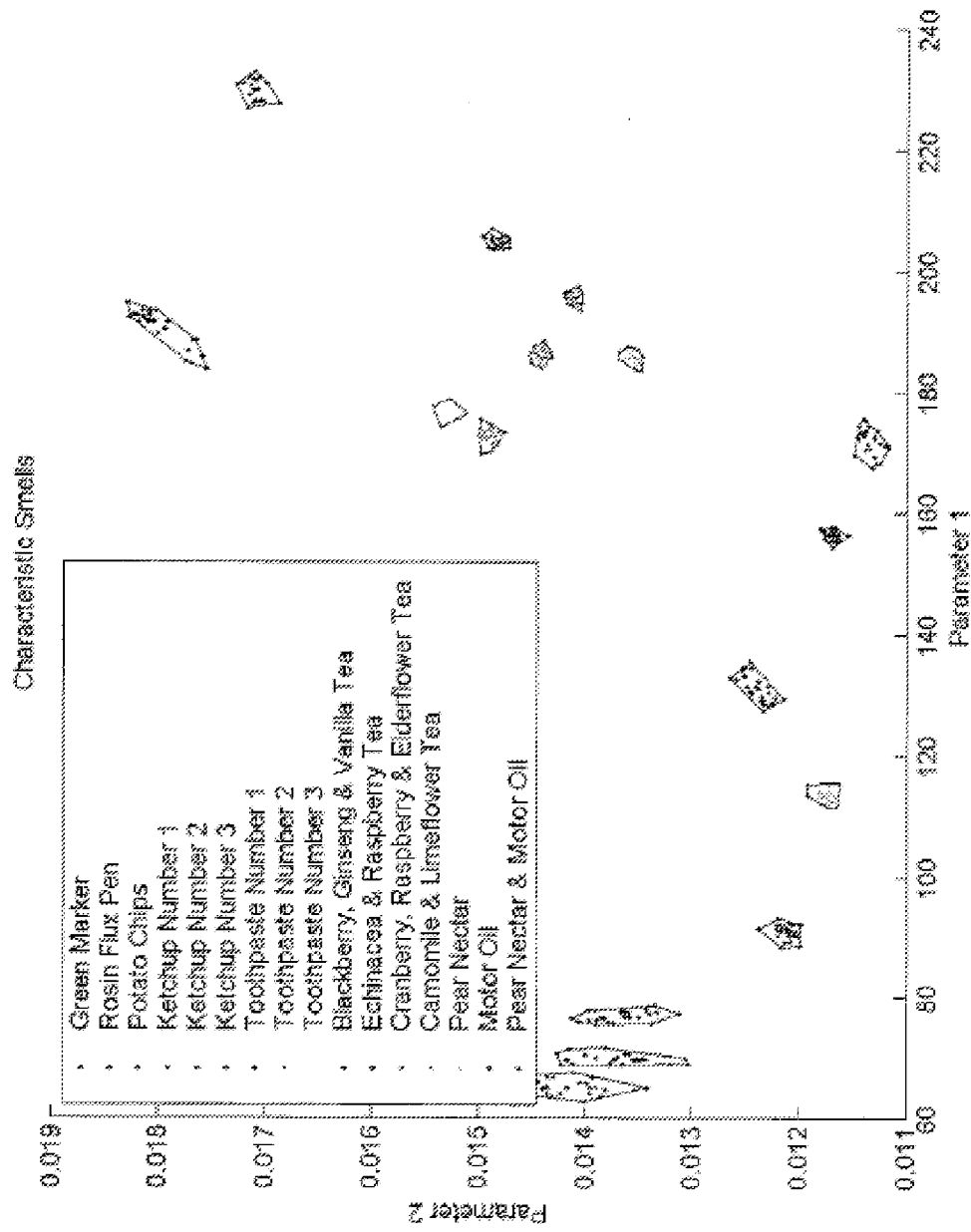
FIGS. 11 to 14 show scatter plots obtained from various samples of different substances using the method of the present disclosure.
Figure 12:
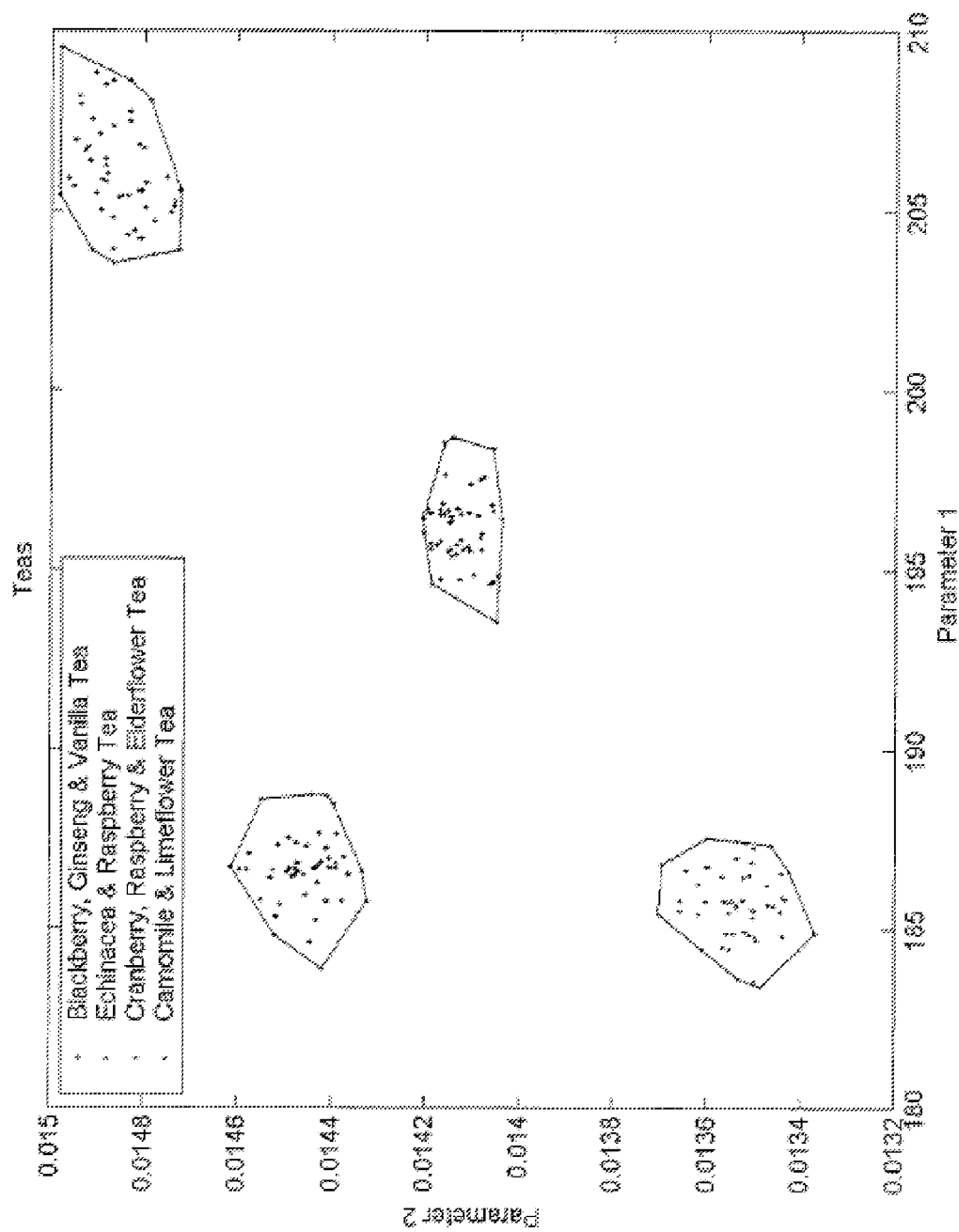
Figure 13:
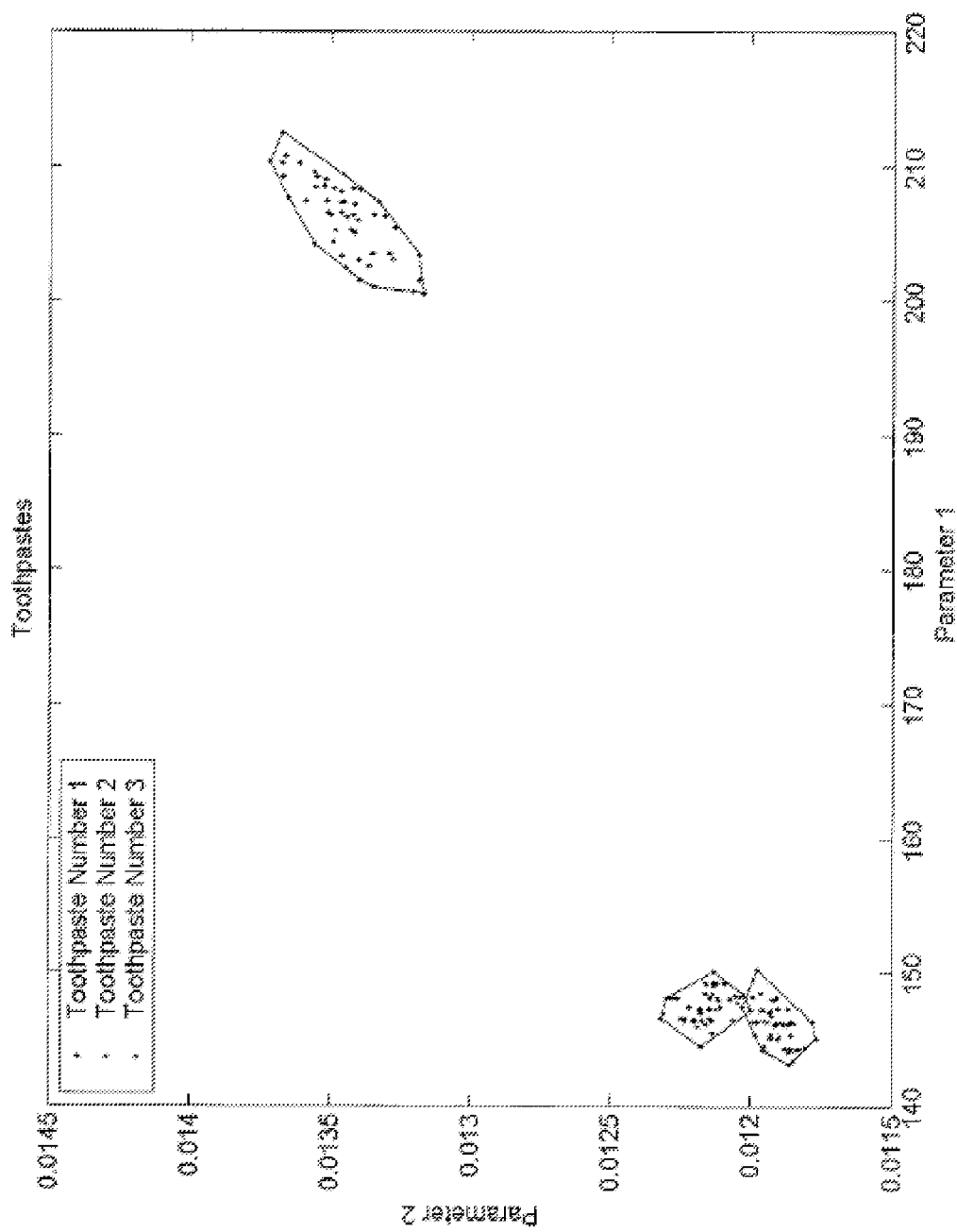
Figure 14:
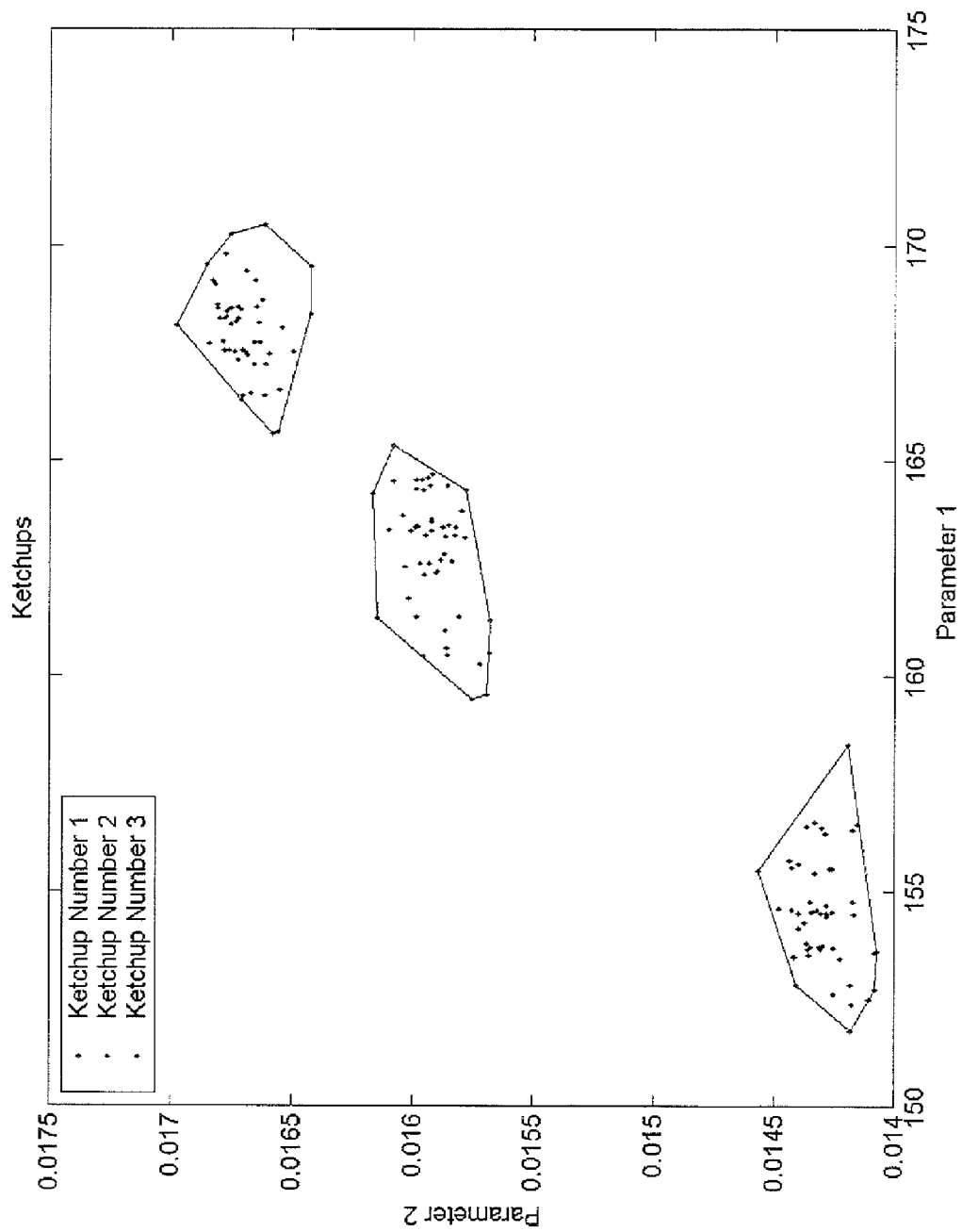

FIGS. 11 to 14 show test results obtained from further experiments. The plotting of data differs in these Figures, in that each peak is plotted on a graph showing variance against amplitude. It can be seen that multiple peaks from the same sample cluster into groups, and that each group (representing a different sample) can be easily distinguished. FIG. 11 shows various samples; FIG. 12 compares different types of herbal tea; FIG. 13 compares different varieties of toothpaste; and FIG. 14 compares different types of ketchup.

Figure 15:
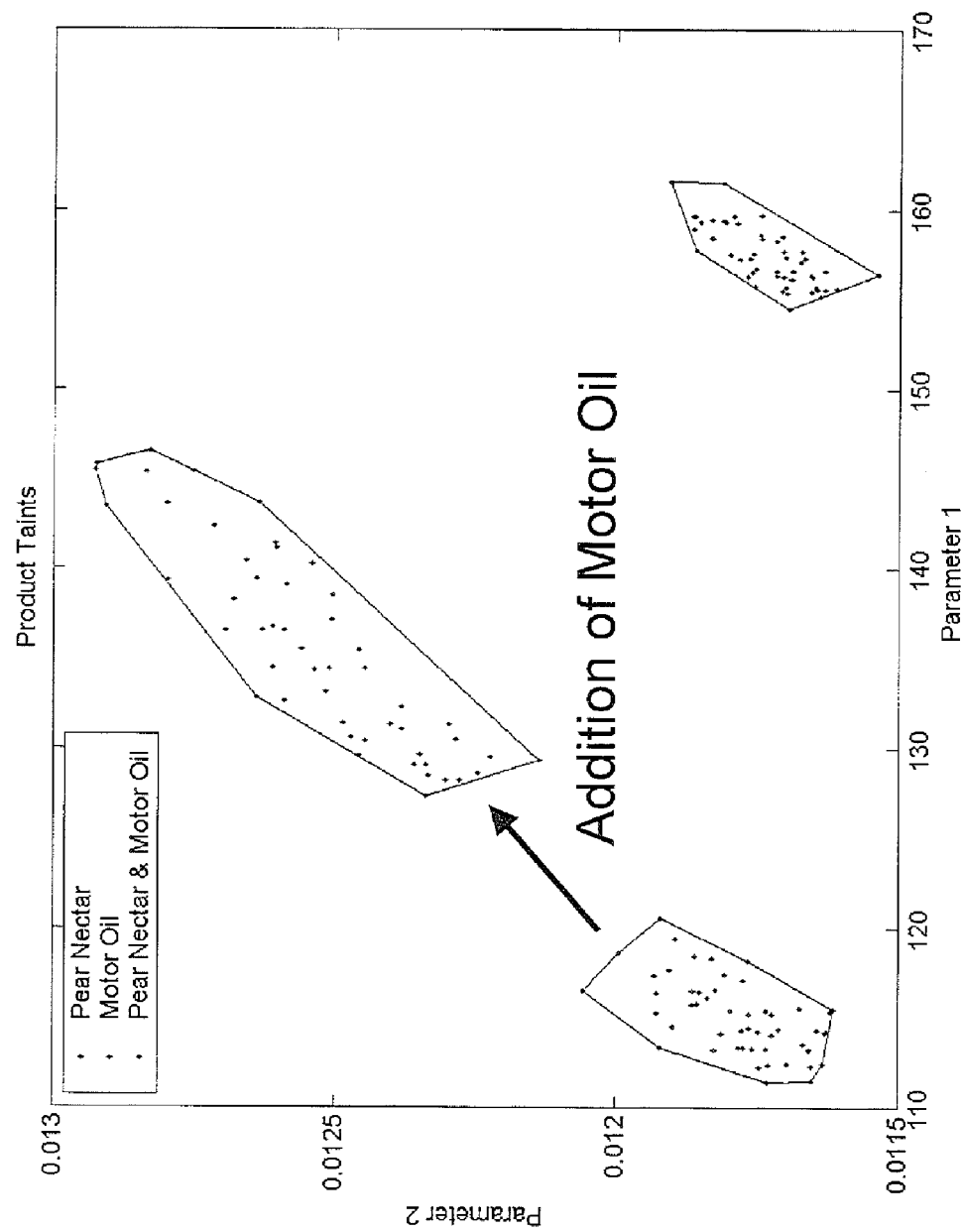
FIG. 15 shows a scatter plot demonstrating the potential use of the present disclosure in quality control of product manufacturing.

An example of a practical application of the device is illustrated in FIG. 15. This is based on a case study of taints in a food manufacturing process. As reported in M. M. Mossoba, Ed., Spectral Methods in Food Analysis: Instrumentation and Applications, Marcel Dekker, New York, N.Y., 1998, in one case consumers reported a smell similar to natural gas in pear and apricot nectar products, consumption of which may be followed by nausea. Inspection of the manufacturing plant identified an oil leak above the filling line, with some of the oil having entered cans on the filling line.

FIG. 15 compares spectra from pear nectar and motor oil separately, and combined pear nectar and motor oil. The key result is that the combined sample can easily be distinguished from the unadulterated pear nectar sample, confirming that embodiments of the present disclosure may be used for quality control of manufacturing processes. It is also interesting to note that the combined sample is very different from either of the separate samples; this again confirms that the sensitivity of the technique is generally not sufficient to identify specific components of a chemical mixture, but is ideally suited to detecting changes in samples over time.

Thus, we have shown that the method described herein can be used for simple change detection. Very simple algorithms and low processing power are required. The technique has the ability to discriminate between changes in composition and in concentration. Substance identification is possible where there are a reduced number of odour choices, or where the odours are suitably different, or where a single odour dominates, or where the background is regular and well characterized.

Figure 17:
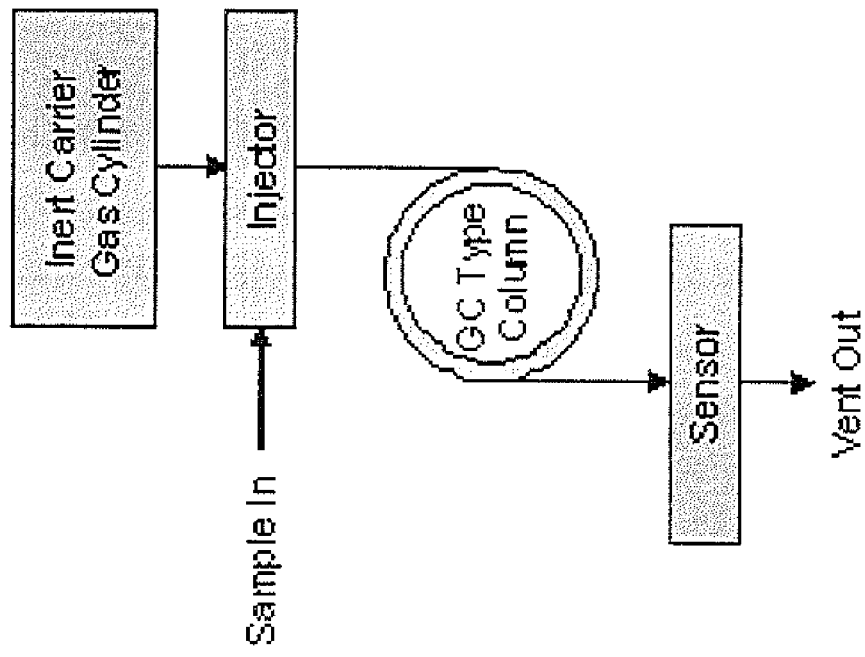
FIG. 17 shows a schematic of the present disclosure in combination with a gas chromatography (GC) device.
Figure 18:
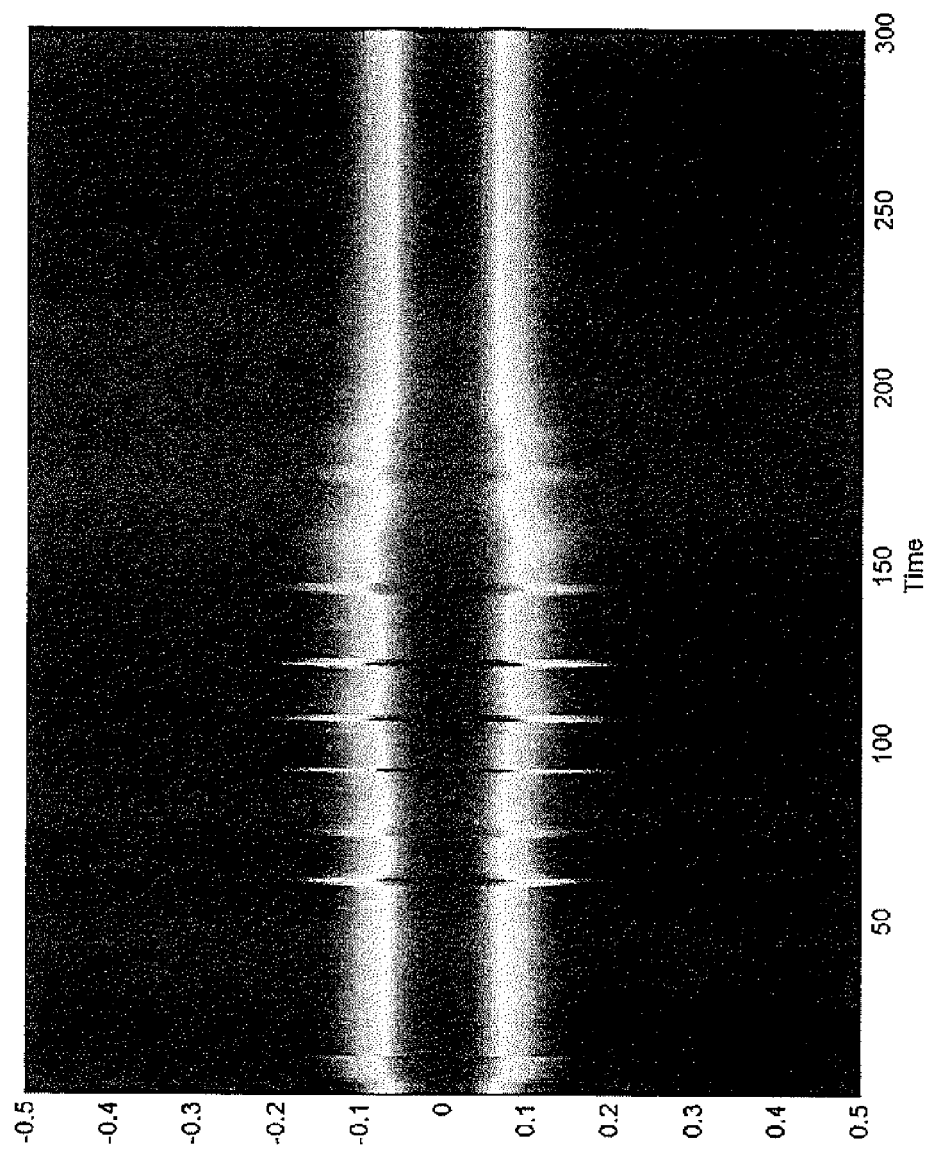
FIG. 18 shows a sample plot obtained from the present disclosure in combination with GC.

The methods and systems disclosed herein may be combined with gas chromatography techniques. Using embodiments of the present disclosure as a detector might result in a smaller and simpler GC system. If UV ionization is used to eliminate ionization of background air, it might be possible to deduce ion mobility from peak shape. Alternatively, or in addition, the present method might be a suitable pre-filter for a mass spectrometer. The very low flow rate requirement of embodiments of the present disclosure might simplify the pneumatics of GC, perhaps eliminating the need for a split flow. The detector's enhanced selectivity might permit isothermal operation or the use of shorter columns. Isothermal operation would eliminate the need for a bulky oven, reducing size and power consumption. A shorter column would reduce analysis times. A schematic of GC operation in combination with an embodiment of the present disclosure is shown in FIG. 17 (the detector is indicated as "Sensor"). Data from a GC analysis is shown in FIG. 18. The Figure shows a series of scans over time. The peak height has been normalized to accentuate changes in peak width. Sudden changes in width indicate the presence of an analyte in the GC effluent. Peaks become wider with decreasing mobility analytes. The signal from background air is continuous and independent of time; it can be subtracted out to highlight changes. High mobility solvent signal dominates at the beginning of the scan, resulting in a narrow peak width at the start.

In other embodiments, it is believed that the method and devices of the disclosure can be a suitable pre-filter for a mass spectrometer (MS). It would be useful for removing contaminants from the sample stream into the MS that interfere with the signal of the target analyte during a normal MS analysis; for example in proteomics research. In this configuration the sensor may not have a detector electrode; the sample simply passes through to the MS for analysis, the purpose of the sensor being to act as a simple filter. Alternatively, a detector electrode may be included so that some of the ion signal is incident on the electrode and some passes through to the MS; this configuration allows simultaneous collection of sensor and MS spectra. Selection occurs as the voltage applied across the filter electrodes is varied, allowing only substances with ion mobilities below the corresponding threshold value to pass through to the MS.

If coupled with UV ionization, in particular vacuum ultraviolet (VUV) ionization, embodiments of the present disclosure provide all of the information of a conventional PID (photoionization detector) plus some extra, albeit crude, information on ion mobility. PID provides a simple amplitude signal, whereas embodiments of the present disclosure provide amplitude plus width, kurtosis and other statistical parameters related to the ion mobility information content extracted. The additional information might provide for improved performance or ease of use, for example by enabling the user to have greater confidence that the substance detected is really what the user thinks it is (i.e. it has a peak width consistent with what would be expected for the target substance); or by enabling the user to better calculate concentration based upon whether the peak shape indicates a single substance dominates or not (using kurtosis and peak width measurements).

Further, embodiments of the present disclosure have a number of advantages over alternative methods. It is a small, low cost, low power, simple solution. Only three components are needed for the preferred embodiment: microcontroller chip, TIA op-amp and ion flow channel. A compact and highly integrated system can be developed, perhaps within a package the size of a traditional electrochemical cell. Efficient ion transmission means that lower flow/ionization source activities are required. The device can directly analyze raw air, so the pneumatics is greatly simplified. It may run at low voltage (5V or less).

Figure 16:
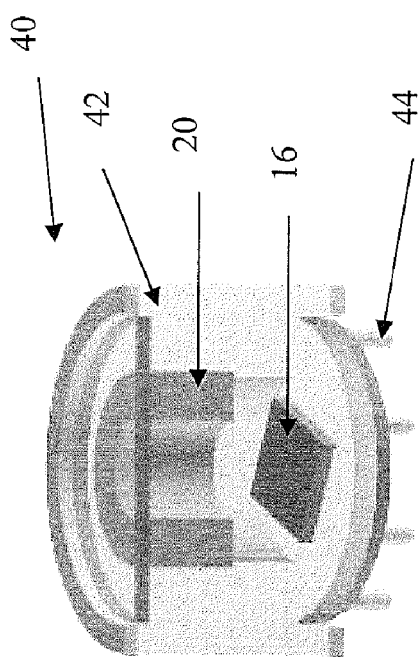
FIG. 16 shows a sensor module which may form an embodiment of the present disclosure.

An illustration of an exemplary sensor device according to the disclosure is shown in FIG. 16. The device 40 includes a housing 42, an ionization source 20, a chip with ion flow channel 16, and a base 44 with integrated detector electrode and electronics. The base 44 includes a number of pins for connection to a conventional circuit board.

In a simple embodiment, there is no user interface whatsoever. This has the benefit of needing no configuration; the device may be preconfigured to provide simple alarms on change events. A more complex embodiment may include a graphical user interface, graphical configuration page, plots of reading histories, and complex alarms on event sequences.

It will be apparent that various modifications and variations may be made to the methods and devices described herein, without departing from the scope of the disclosure.

What is claimed is:

1. A method for monitoring chemical species in a gas flow, the method comprising:
   a) ionizing a sample of gas;
   b) passing the ionized gas sample through an ion flow channel along a longitudinal axis thereof, the channel being subject to a generated DC electric field which is transverse to the longitudinal axis of the channel;
   c) monitoring over time the electric current at a detector electrode arranged to intercept at least some of the ions so as to generate a signal from the detector electrode, wherein the detector electrode detects ions which flow parallel to the longitudinal axis of the ion flow channel and transverse to the DC electric field, with a change in current being indicative of a change in the composition of chemical species in the gas flow; and
   d) providing a characteristic of the sample of gas by comparing the signal from the detector electrode with a magnitude of the generated DC electric field at the detector electrode, whereby a resulting electric current versus a voltage graph of the detector electrode is used as a characteristic of the sample of gas.

2. The method of claim 1, further comprising varying the DC field over time and comparing monitored electric current with the DC voltage.

3. The method of claim 1, wherein the DC field is repeatedly cycled over time.

4. The method of claim 3, further comprising comparing successive cycles with one another to monitor for changes in ion composition.

5. The method of claim 1, wherein the step of detecting current flow includes detecting ions which have passed completely through the ion flow channel.

6. The method of claim 5, wherein the step of detecting current flow includes detecting ions which do not pass through the ion flow channel.

7. The method of claim 1, wherein ionizing the sample of gas includes subjecting the sample to ionizing radiation.

8. The method of claim 1, wherein passing the ionized sample through the flow channel includes driving the sample flow with a pump.

9. The method of claim 8 wherein the pumping is continuous.

10. The method of claim 1, further comprising processing data relating to the monitored current to obtain further information on the ions.

11. The method of claim 1, further comprising alerting a user to a variation in the monitored current.

12. A method for monitoring changes in odours, comprising monitoring chemical species in a sample in accordance with the method of claim 1.

* * * * *